US006719990B2

United States Patent
Patel et al.

(10) Patent No.: US 6,719,990 B2
(45) Date of Patent: Apr. 13, 2004

(54) NON-AQUEOUS INJECTABLE FORMULATIONS FOR EXTENDED RELEASE OF SOMATOTROPIN

(75) Inventors: Kanaiyalal R. Patel, St. Louis, MO (US); Yunhua N. Jeng, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/789,392

(22) Filed: Feb. 21, 2001

(65) Prior Publication Data

US 2001/0046954 A1 Nov. 29, 2001

Related U.S. Application Data

(60) Provisional application No. 60/184,625, filed on Feb. 24, 2000.

(51) Int. Cl.[7] ............................................... C07K 15/00
(52) U.S. Cl. ........................... 424/422; 514/2; 514/12; 514/21; 530/397; 530/399; 530/362; 530/363; 424/422; 424/424; 424/426; 424/463
(58) Field of Search ................. 514/2, 12, 21; 424/422, 424, 426, 463, 471, 472, 473

(56) References Cited

U.S. PATENT DOCUMENTS

| | | | | |
|---|---|---|---|---|
| 4,816,568 A | * | 3/1989 | Hamilton | ............ 530/399 |
| 4,857,506 A | | 8/1989 | Tyle | ............ 514/12 |

(List continued on next page.)

FOREIGN PATENT DOCUMENTS

| | | |
|---|---|---|
| EP | 0 216 485 | 4/1987 |
| EP | 0 278 103 A | 8/1988 |
| EP | 0303746 * | 2/1989 .......... A61K/37/36 |
| EP | 0 374 120 A | 6/1990 |
| EP | 0 523 330 A1 | 1/1993 |
| EP | 913177 | 5/1999 |
| WO | WO 89 09614 A | 10/1989 |
| WO | WO 93/12812 | 7/1993 |
| WO | WO 93/13792 | 7/1993 |
| WO | WO 93/19773 | 10/1993 |
| WO | WO 97/03692 | 2/1997 |
| WO | WO 97/29767 | 8/1997 |
| WO | WO 98/29131 | 7/1998 |
| WO | WO 00/13674 | 3/2000 |

OTHER PUBLICATIONS

Katakam, Manohar: *Use of non–ionic surfactants to stabilize recombinant human growth hormone and to develop its sustained release formulation*, Diss. Abstr. Int., vol. 57, No. 5, 1996, p. 3149.

Primary Examiner—Christopher Tate
Assistant Examiner—Roy Teller
(74) Attorney, Agent, or Firm—Gary M. Bond; Howrey Simon Arnold & White, LLP

(57) ABSTRACT

The present invention provides compositions which allow for the extended release and enhanced bioavailability of biologically-active polypeptides following parenteral delivery to an animal. More particularly, it concerns compositions comprising biologically-active somatotropin formulated for extended release, methods of preparing these compositions, and methods of using the same. These compositions comprise somatotropin, a bioavailability-enhancing constituent (BEC), and a substantially non-aqueous, hydrophobic excipient. The BEC may comprise (i) amino acids or amino acid derivatives, such as histidine-HCl; (ii) hydroxamate derivatives, such as histidine hydroxamate or suberohydroxamic acid; (iii) non-reducing carbohydrates, such as trehalose or trehalose octaacetate; (iv) oxo-acid salts, such as a mixture of monobasic and dibasic sodium phosphate; or (v) a mixture of two or more compounds from within the foregoing classes (i)–(iv).

11 Claims, 6 Drawing Sheets

U.S. PATENT DOCUMENTS

| | | | |
|---|---|---|---|
| 4,917,685 A | 4/1990 | Viswanathan et al. | 604/891.1 |
| 4,977,140 A | 12/1990 | Ferguson et al. | 514/12 |
| 5,034,229 A | 7/1991 | Magruder et al. | 424/422 |
| 5,037,420 A * | 8/1991 | Magruder et al. | 604/892.1 |
| 5,096,885 A | 3/1992 | Pearlman et al. | |
| 5,219,572 A | 6/1993 | Sivaramakrishnan et al. | 424/438 |
| 5,356,635 A | 10/1994 | Raman et al. | 424/484 |
| 5,359,030 A | 10/1994 | Ekwuribe | |
| 5,399,489 A | 3/1995 | Krivi | 435/69.4 |
| 5,438,040 A | 8/1995 | Ekwuribe | |
| 5,474,980 A * | 12/1995 | Mitchell | 514/12 |
| 5,520,927 A | 5/1996 | Kim et al. | 424/450 |
| 5,607,691 A | 3/1997 | Hale | |
| 5,612,315 A | 3/1997 | Pikal et al. | 514/21 |
| 5,631,227 A | 5/1997 | Harbour | |
| 5,681,811 A | 10/1997 | Ekwuribe | |
| 5,739,108 A | 4/1998 | Mitchell | 514/12 |
| 5,744,163 A | 4/1998 | Kim et al. | 424/489 |
| 5,773,588 A | 6/1998 | Owsley | |
| 5,801,141 A * | 9/1998 | Steber | 514/2 |
| 5,849,704 A | 12/1998 | Sørensen et al. | 514/12 |
| 5,972,370 A | 10/1999 | Eckenhoff | |
| 5,986,073 A | 11/1999 | Storrs et al. | 530/419 |
| 6,086,918 A | 7/2000 | Stern | |
| 6,162,258 A | 12/2000 | Scarborough | |

* cited by examiner

NON-AQUEOUS INJECTABLE FORMULATIONS FOR EXTENDED RELEASE OF SOMATOTROPIN

This application claims priority to Provisional Application Ser. No. 60/184,625 filed Feb. 24, 2000.

BACKGROUND OF THE INVENTION

1. Field of the Invention

The present invention relates to the field of biologically-active somatotropin compositions. More particularly, it concerns biologically-active compositions of somatotropin formulated for extended release into the bloodstream of an animal following parenteral administration, methods of preparing these compositions, and methods of using the same.

2. Technical Problem Addressed by the Invention

Although prolonged activity of some biologically active (bioactive) polypeptides can be achieved by parenterally administering only very small doses, others are required in sufficient serum concentrations and/or have such a short half-life in serum that a substantial dose must be administered to provide the desired biological effect over an extended time such as a week or longer. Somatotropins (growth hormones) are an example of such polypeptides.

To prevent undesirably rapid release into an animal's bloodstream, certain polypeptides have been parenterally administered in liquid vehicles which may optionally contain hydration retardants (antihydration agents) or in association with metals or metal compounds that further lower their solubility in body fluids. To avoid the need for unacceptably large quantities of such a vehicle, and for other reasons including superior prolonged release performance, it is advantageous to employ substantial concentrations of the polypeptide in the vehicle, e.g., as shown in U.S. Pat. Nos. 5,739,108 to James C. Mitchell, 4,977,140, assigned to Eli Lilly, 5,520,927, assigned to Lucky, Ltd., and 5,744,163, assigned to LG Chemicals Ltd. However, there has been a need to improve the efficiency with which such polypeptides are released into the animal's bloodstream in a biologically active form ("bioavailability") and/or, in some utilities, their effectiveness in providing the desired physiological response in the animal ("efficacy"). Each of these factors can substantially affect the amount of the polypeptide that must be administered to achieve the desired biological effect, and consequently, the cost of each administration. Typically, polypeptides such as somatotropins are made in prokaryotic organisms that have been transformed using recombinant DNA, such that even small quantities are very expensive to produce in the pure forms required for product safety and regulatory approval.

3. Description of Related Art

There is currently a substantial body of work which addresses the need for protein formulations which provide for extended release of biologically active polypeptides, including somatotropins. This body of work includes a number of publications describing the use of various stabilizing compounds and excipients. Furthermore, various methods of and devices for administering the bioactive compositions have also been reported in the existing art. Exemplary publications which address this technological problem include the following:

Christensen et al., WO 97/03692, discloses a formulation of growth hormone with zinc, and optionally lysine or calcium, ions. The formulation can contain an excipient such as a disaccharide, a polysaccharide, or a sugar alcohol. Growth hormone so formulated showed resistance to deamidation.

Ferguson et al., U.S. Pat. No. 4,977,140, discloses a sustained release formulation comprising bovine somatotropin in a carrier comprising a wax (about 1%–20% by weight) and an oil (about 80%–99% by weight). On injecting into a dairy cow, the formulation led to greater milk production for 28 days.

Hamilton et al., U.S. Pat. No. 4,816,568, discloses compositions of animal growth hormones and stabilizers. The stabilizers are soluble in aqueous solutions, and generally are very polar. The stabilizers taught include polyols, amino acids, amino acid polymers with charged side groups at physiological pH, and choline derivatives. An aqueous formulation of the composition can be formed by (i) dispersing the stabilizer in an aqueous solution and (ii) subsequently adding the growth hormone. A solid formulation can be formed by (i) mixing the stabilizer and the growth hormone, (ii) optionally adding adjuvants, binders, etc. to the composition, and (iii) compressing the composition to form a tablet or pellet.

Kim et al., U.S. Pat. No. 5,520,927, discloses a parenterally administered, slow releasing bioactive pharmaceutical composition comprising somatotropin, at least one tocopherol compound, and a release delaying agent.

Kim et al., U.S. Pat. No. 5,744,163, discloses a formulation for the sustained release of animal growth hormone. The formulation comprises coating somatotropin containing pellets with a film of biodegradable polymer and a poloxamer.

Magruder et al., U.S. Pat. No. 5,034,229, discloses a device for delivering a beneficial agent, e.g. a growth hormone, to an animal. The device can also deliver a polyol as a viscosity modulating means.

Martin, EP 0 216 485, discloses a method of preparing growth hormones complexed with transition metals. Methods for promoting growth in animals by treating them with transition metal complexed growth hormones are also described.

Mitchell, U.S. Pat. No. 5,739,108, discloses extended-release formulations of bioactive polypeptides comprising the polypeptide at from about 10% by weight to about 50% by weight in a dispersion in a biocompatible oil. The polypeptide can be associated with a non-toxic metal or metal salt. The formulation can also comprise an antihydration agent, such as aluminum monostearate.

Pikal, et al., U.S. Pat. No. 5,612,315, discloses formulations for the parenteral administration of human growth hormone comprising human growth hormone, glycine, and mannitol. The disclosed formulations are described as providing stabilization against protein aggregation.

Raman et al., U.S. Pat. No. 5,356,635, discloses a sustained release composition comprising a biologically active agent, e.g. somatotropin; a biodegradable, amorphous carbohydrate glass matrix, throughout which the e.g. somatotropin is dispersed; and a hydrophobic substance. The amorphous carbohydrate glass matrix comprises an amorphous carbohydrate and a recrystallization retarding agent, and makes up from about 60% by weight to 90% by weight of the composition. The composition is solid down to at least about 18° C.

Raman et al., WO 93/13792, discloses an implantable device comprising a transition metal-somatotropin complex in combination with a transition metal-solubilizing substance. The transition metal can be zinc, manganese, or copper. The metal-solubilizing substance can be an amino acid. Sucrose can be used to stabilize the somatotropin. The device can comprise silicone tubing or wax.

Seely et al., WO 93/19773, discloses aqueous solutions comprising (i) a lyophilized somatotropin composition comprising somatotropin and arginine HCl and (ii) a diluent comprising EDTA, nonionic surfactant, and optionally buffer or a non-buffering agent such as sucrose or trehalose.

Sivaramakrishnan et al., U.S. Pat. No. 5,219,572, discloses a device for controlled release of macromolecular proteins, e.g. somatotropin. The device comprises a water-soluble outer capsule completely surrounding an inner compartment containing non-uniform beadlets. The beadlets comprise a wax shell which surrounds a core matrix. The core matrix comprises e.g. somatotropin and optionally excipients, stabilizers, binders, and the like, e.g. magnesium stearate or sucrose. Upon dissolution of the outer capsule in the fluid environment in an animal, the beadlets are exposed to the fluid environment, and rupture at various times after exposure.

Sørensen et al., WO 93/12812, teaches that growth hormone can be stabilized by the presence of histidine or a histidine derivative. If the growth hormone is lyophilized, the composition can also comprise a bulking agent, i.e. sugar alcohols, disaccharides, and mixtures thereof.

Sørensen et al., U.S. Pat. No. 5,849,704, discloses a pharmaceutical formulation comprising a growth hormone and histidine or a derivative of histidine as an additive or buffering substance added to provide stability against deamidation, oxidation or cleavage of the peptide bonds in the growth hormone. Also disclosed is that crystallization of growth hormone in the presence of histidine or a derivative thereof gives rise to a higher yield of crystals having higher purity than known methods.

Steber et al., EP 0 523 330 A1, discloses a compacted, indented, partially-coated, implantable composition comprising a biologically active polypeptide (e.g. somatotropin); a fat, wax, or mixture thereof; and a sugar (e.g. mono-, di-, or trisaccharides).

Storrs, et al. U.S. Pat. No. 5,986,073, discloses a method for purifying and recovering biologically active somatotropin monomers. This work is based on the discovery that somatotropin monomers and somatotropin oligomers having overlapping isoelectric points may nevertheless be separated by selective precipitation over a very narrow pH range. Undesirable impurities are removed by this process and the purified somatotropin monomers recovered are suitable for parenteral application to target animals without further purification.

Tyle, U.S. Pat. No. 4,857,506, discloses a multiple water-in-oil-in-water emulsion for the sustained release of a growth hormone. The growth hormone is dispersed in an internal aqueous phase; the internal aqueous phase is dispersed in a water-immiscible liquid or oil phase; and the water-immiscible phase is dispersed in an external aqueous phase. The internal aqueous phase can include up to 40% by weight polyol, glycol, or sugar.

Viswanathan et al., U.S. Pat. No. 4,917,685, discloses a delivery device for a stabilized animal growth hormone. The device comprises a wall which surrounds and defines a reservoir. At least a portion of the wall is porous, to allow passage of growth hormone and stabilizer. The growth hormone and stabilizer formulation is substantially that disclosed by Hamilton et al., described above.

Despite the efforts described in the publications summarized above, there is still room for significant improvement of the technology. The present invention satisfies this need by providing improved, sustained release formulation of a somatotropin which has the advantages of providing both higher and more sustained levels of somatotropin in the serum of animals treated with these formulations.

The art summarized above discloses formulations in which the ingredients are present as solutes in aqueous solutions or as solids in tablets or pellets. The present invention describes non-aqueous injectable formulations in which dry solids are suspended in an non-aqueous carrier. Treatment of cattle, with the formulations described herein, results in surprisingly increased milk production and extended response to the new formulations in those animals.

SUMMARY OF THE INVENTION

The present invention provides for a composition of matter, which provides both for higher serum levels of somatotropin ("ST") and for a prolonged maintenance of those higher serum ST levels, compared to known formulations containing the same dose of somatotropin. Furthermore, these formulations have been demonstrated to also have superior efficacy for inducing weight gain and milk production when compared with currently available formulations containing the same amount of somatotropin. The ST formulations of the present invention have been demonstrated to be particularly effective for sustaining elevated milk production, compared to previously available formulations.

The formulations of the present invention provide for compositions of matter which comprise somatotropin and a bioavailability-enhancing constituent (BEC, where "bioavailability" is the net result of the release, absorption, elimination, degradation and other physiological processes for a substance). The bioavailability-enhancing constituent can be comprised of one or more of the following: (a) an amino acid, amino acid derivative such as histidine-HCl, or an amino acid polymer, such as polyhistidine; (b) an hydroxamate, such as suberohydrxamic acid, or hydroxamate derivative, such as histidine hydroxamate; (c) a non-reducing carbohydrate, such as a polyol or polyol ester; (d) the salt of an oxo-acid, such as monobasic sodium phosphate or dibasic sodium phosphate or a mixture of monobasic and dibasic sodium phosphate; or (e) imidazole or imidazole-HCl.

In various embodiments of the invention the ST and the BEC are suspended in a substantially non-aqueous hydrophobic carrier which yields a formulation which is fluidly injectable at the body temperature of the animal to be injected (typically 37–39° C.), and preferably injectable at 25° C. The compositions of the instant invention may be of any viscosity which is compatible with the present invention. In a preferred embodiment the viscosity of the composition is between about 500 and about 10,000 centipoise at $141^{-1}$ s. An exemplary carrier considered for use in the present invention is a mixture of 95% sesame oil and 5% aluminum monostearate According to the present invention the ST used in the formulations may be from any origin which is suitable for use with the invention, including, but not limited to, native and/or recombinant bovine, porcine, equine, or human somatotropin. The ST used may be present in an essentially pure form or may be combined with another substance (e.g., the ST used may be in the form of a zinc salt or zinc complex of ST).

In an alternative embodiment, where the BEC is an amino acid, amino acid derivative, hydroxamate or hydroxamate derivative, the BEC comprises from about 0.5% to about 30%; preferably from about 1% to about 20%; and even more desirably from about 2% to about 10% of the composition.

According to another embodiment of the present invention, when the BEC used is a non-reducing carbohydrate it comprises from about 1% to about 50%, of the composition, preferably from 5% to 20%, and even more preferably from 10% to 15% of the composition.

In yet another embodiment of the present invention, when the BEC is the salt of an oxo-acid, the BEC comprises from about 0.5% to about 30% of the composition, preferably from about 1% to about 20%, and even more preferably from about 2% to about 10% of the composition.

The present invention also provides a method of preparing the described compositions of matter. According to such an embodiment of the present invention the ST is provided as a lyophilized dry solid (for an example of preparing the lyophilized ST see U.S. Pat. No. 5,013,713, which is incorporated herein by reference), the BEC is likewise provided as a dry solid. The method for preparing these compositions of matter comprises mixing the dry, solid BEC with the hydrophobic carrier, to produce a first suspension and then mixing the lyophilized, dry, solid ST with the first suspension to produce a second suspension.

Another embodiment of the present invention provides a method for inducing improved weight gain or elevated milk production in a mammal. This method comprises injecting an ST formulation of the present invention into the target mammal.

Yet another embodiment of the present invention provides a method for sustaining the elevated milk production response in a lactating mammal. This method comprises injecting the target mammal with a biocompatible ST formulation according to the present invention, wherein the ST present in the formulation is active in the target mammal.

According to the present invention these compositions and methods may be better understood by a review of the detailed description in conjunction with the drawings, which serve to facilitate the further illustration of certain aspects and/or certain embodiments of the invention.

DEFINITIONS

The following definitions are provided in order to aid those skilled in the art to understand the detailed description of the present invention.

Throughout the specification, unless otherwise indicated, percentages of compositions are by weight and temperatures are in degrees Celsius (° C.).

As used in the specification and claims, the term "substantially non-aqueous" means essentially anhydrous or containing water in such low proportion that it does not intolerably accelerate release of the polypeptide in the animal. Although this proportion of water may vary with each composition of the invention it is most commonly less than about 2% and most typically less than about 1%.

The term "non-toxic" as used herein refers to components of compositions that are reasonably safe and/or innocuous when used in appropriate amounts and under appropriate conditions in parenteral administration of such compositions as are described herein.

The term "biologically-active" or "bioactive" polypeptide or protein (e.g. somatotropin) is used herein to describe a polypeptide or protein, which following appropriate parenteral administration to an animal, has a demonstrable effect on a biological process of that animal. The effect may be hormonal, nutritive, therapeutic, prophylactic, or otherwise, and may mimic, complement, or inhibit a naturally occurring biological process. Although there is a vast array of potentially regulatable biological activities or processes, the following are mentioned as exemplary: stimulation of growth, stimulation of lactation, stimulation of egg or offspring production, and enhancement of the efficiency of feed usage.

The term "biocompatible", as used herein, refers to substances which have no intolerable adverse effect on the somatotropin, the animal, or, in the case of animals whose products enter the food chain, the consumers of such products.

"Sustaining elevated milk production response" or "sustained elevated milk production response", as used herein, refers to the ability of lactating animals to maintain an elevated level of milk production, over a period of time, despite decreasing serum levels of somatotropin.

DESCRIPTION OF PREFERRED EMBODIMENTS

Figure 1:
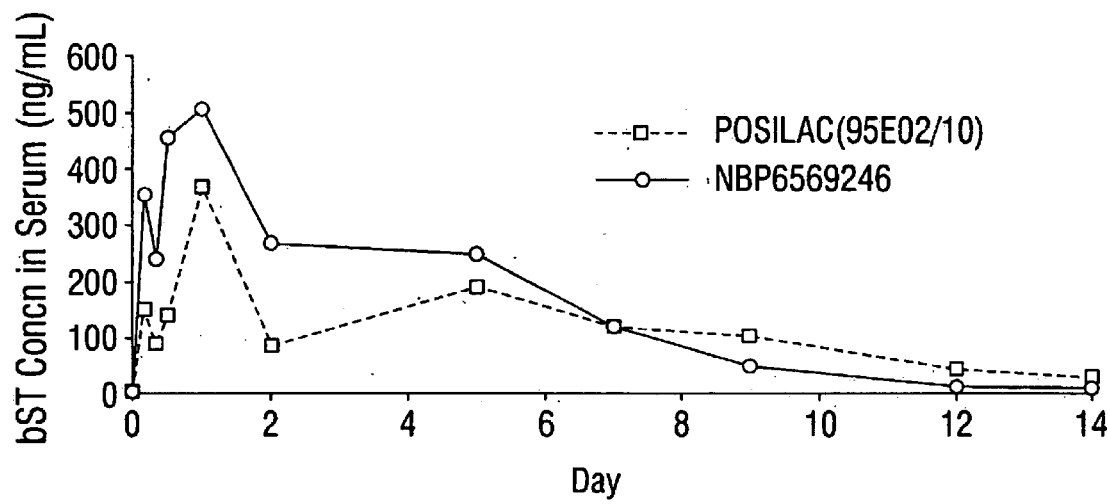
FIG. 1 is a graph showing the serum bovine somatotropin ("bST") levels over time in rodents treated with a bST composition which contained histidine-HCl as the bioavailability-enhancing constituent.

The present invention provides an injectable (or otherwise parenterally administerable) enhanced bioavailability formulation comprising: (i) a dry solid native or recombinant protein growth hormone (GH, synonymous with somatotropin, herein sometimes abbreviated as ST), and (ii) a dry, solid bioavailability-enhancing constituent (BEC). Both the ST and BEC are suspended in an excipient comprised of a substantially non-aqueous oil, fat, or other hydrophobic substance that is at least partially liquid to creamy and/or biodegradable in an animal at the animal's body temperature and which is biocompatible with the animal.

Somatotropins from man and from the common domestic animals are proteins of approximately 191 amino acids, which are synthesized and secreted by the anterior lobe of the pituitary gland. Full length human ST (hST) consists of 191 amino acids. ST is a key hormone involved in the coordination of somatic growth through the regulation of the metabolic processing of proteins, carbohydrates, and lipids. A major known effect of ST is the promotion of growth in organ systems which include, but are not limited to, the skeleton, connective tissue, muscles, and viscera such as the liver, intestine, and kidneys.

Growth hormones suitable for use in the present invention include, but are not limited to, somatotropins from human, bovine, equine, ovine, porcine, caprine, and avian sources. Preferably the ST is human, equine, bovine, or porcine ST. Even more preferably the ST is bovine or human ST (bST).

Somatotropin for use in the present invention can be obtained by extraction and subsequent concentration from the pituitary glands of various animals. Alternatively, ST may be produced using recombinant DNA techniques which are well understood and commonly used by those skilled in the art.

Somatotropins prepared using recombinant DNA techniques suitable for use according to the present invention may be produced by genetically transformed microorganism such as *E. coli*, or other bacteria, or by yeasts. Recombinant ST may also be produced by tissue culture or by a transgenic multicellular organism.

Somatotropins produced using molecular biological techniques may have an amino acid sequence identical to naturally occurring somatotropin. Alternatively, the somatotropin used may be an ST analog comprising one or more variations in amino acid sequence with respect to the native hormone. These amino acid variations may provide enhanced biological activity or some other biological or logistical advantages.

ST is usually synthesized in its native organism as an inactive precursor molecule which is processed to the mature, active form of the hormone via cleavage of an N-terminal signal peptide (26 amino acids in humans, 27 amino acids in cows). In order to express bioactive ST protein using recombinant DNA technology it may be advantageous to add, change, or delete one or more amino acids from the polypeptide. Such modifications, which do not overly diminish the activity of the ST, or make it biologically incompatible with the animal to be treated, are useful in the present invention. For example it may be useful to produce an ST polypeptide which contains a methionine residue at its N-terminus (N-terminal to the phenylalanine residue which is typically the first amino acid in the mature, active form the native hormone), resulting from microbial translation of the AUG start codon in a recombinant gene for the polypeptide (this form of ST is known as N-methionyl-ST). Another derivative envisioned for use in the present invention is N-alaninyl-ST, which is similar to N-methionyl-ST except it begins with an N-terminal alanine residue (See Krivi U.S. Pat. No. 5,399,489, which is incorporated herein by reference) rather than an N-terminal methionine.

According to the various embodiments of the current invention the ST can be administered in a chemically uncombined form. Other embodiments are advantageously carried out using ST in a form which has substantially lower solubility in aqueous environments or animal body fluids than the uncombined ST (e.g. chemically or otherwise combined with another substance). For example, the ST can be predominantly or partially chemically associated with a biocompatible metal, or an ester, amide or other moiety or moieties which aid in providing the desired bioactivity and which do not induce intolerable side effects in the animal treated with the composition. When associated with such a metal, the metal can be present as the metal per se (e.g. as a metal salt of or in a complex with the ST) or in the form of a salt or complex of the metal with one or more other anions.

Although monovalent metals (e.g. sodium or potassium) can be used advantageously in some compositions of this invention, polyvalent metals are preferred. Examples of such polyvalent metals include zinc, iron, calcium, bismuth, barium, magnesium, manganese, aluminum, copper, cobalt, nickel, cadmium and the like. In certain highly preferred embodiments, such metal-associated ST molecules are reaction products of such metals, e.g. in ionic form, with dissolved ST. The ratio of metal to ST may vary depending on the number of active sites of the ST that associate with such metal during the formation process (e.g., it may vary as a function of pH). For instance, metal may be associated with some or all negatively-charged amino acid (e.g. aspartic or glutamic) residues in the ST, or with its carboxy terminus. Some or all of the metal may be associated by any physical or chemical means including, but not limited to, as salt or complex with the ST, occluded within folds, crystals or amorphous shapes of the ST, or associated as a cation bridge between at least two ST molecules.

When the metal is polyvalent, its valence may be only partly chemically associated with the ST polypeptide in some cases, e.g. because of steric hindrance. In such cases, the remaining valence of the metal may be chemically associated with other anions. In many desirable embodiments, the metal is not chemically associated in substantial proportion with other anions that form salts or complexes having low water solubility with said metal. When the metal is partly chemically associated with other anions, such other anions (organic or inorganic) are often desirably selected from those that form water-soluble salts or complexes with that metal, e.g. $Br^-$, $Cl^-$, $I^-$, $SO_4^{2-}$, or $CH_3COO^-$ when the metal is zinc. Monovalent anions, e.g. $Cl^-$, are generally most preferred.

A preferred embodiment of this invention includes somatotropins associated with zinc (ZnST). In some instances, these may contain up to about 5% zinc or more, based on the weight of the somatotropin. To minimize the chance of undesirable injection site responses in the animals, however, it may be desirable for them to contain no more than about 2%, and in some instances no more than about 1% zinc. In preferred embodiments these ZnST molecules contain at least about 0.3% (usually at least about 0.5%) zinc, although lower percentages of zinc may be suitable in some cases.

Examples of other ST salts and complexes useful in this invention include: (i) acid addition salts formed with inorganic acids, e.g., hydrochloric, hydrobromic, sulfuric, phosphoric or nitric; or organic acids, e.g., acetic, oxalic, tartaric, succinic, maleic, fumaric, gluconic, citric, malic, ascorbic, benzoic, tannic, pamoic, alginic, polyglutamic, naphthalenesulfonic, naphthalene-disulfonic or polygalacturonic; (ii) salts and complexes with polyvalent organic cations, e.g. N'-dibenzylethylenediamine or ethylenediamine; and (iii) combinations of two or more of the aforementioned types of salts or complexes, e.g. zinc tannate.

Especially preferred are salts and complexes of zinc, iron, calcium, magnesium, manganese, sodium, potassium and mixtures thereof. Even more preferred, are salts or complexes of zinc, sodium or potassium, with ZnST being most preferred.

In a preferred embodiment of the present invention the bioavailability-enhancing constituent (BEC) comprises one or more substances selected from the following: (a) an amino acid or amino acid derivative, (b) an hydroxamate or hydroxamate derivative, (c) a non-reducing carbohydrate, (d) an oxo-acid salt, or (e) imidazole or imidazole-HCl.

Amino acids and amino acid derivatives which are compatible with and preferred as bioavailability-enhancing constituents for use with the instant invention include, but are not limited to the following: histidine, histidine salts, such as histidine-HCl, histidine derivatives, including polyhistidine and histidine hydroxamate, arginine, lysine, tryptophan, methionine, arginine, glutamic acid, aspartic acid, glycine. The use of histidine-HCl is particularly preferred.

Amino acids or amino acid derivatives can be added in an amount ranging from 0.5 to 30% (w/w) in the formulation. The more desirable range of amino acid or derivative is 1–20% (w/w) and the most preferred range is 2–10% (w/w). In formulations comprising amino acids or amino acid derivatives ST can be added in an amount ranging from 10 to 50% (w/w) in the formulation. The more desirable range for ST is 20–46% and the most preferred range is 32–42% (w/w). Thus, the most preferred non-aqueous injectable formulation preparation, having amino acids or amino acid derivatives, comprises amino acid or derivative in an amount of 0.05 to 0.3 mg (2–10% by weight) per mg of ST (32–42% by weight).

In another embodiment of the present invention the bioavailability-enhancing constituent is a hydroxamate or hydroxamate derivative. Preferred hydroxamates for use as bioavailability-enhancing constituents in the present invention are those which bind metals, particularly, zinc, these include: suberohydroxamic acid, salicly hydroxamic acid, bufexamac acid, and caprylohydroxamic acid.

Hydroxamates or hydroxamate derivatives can be added in an amount ranging from 0.5 to 30% (w/w) in the formulation. The more desirable range of hydroxamates or hydroxamate derivatives is 1–20% (w/w) and the most preferred range is 2–10% (w/w). In formulations comprising hydroxamates or hydroxamate derivatives, ST can be added in an amount ranging from 10 to 50% (w/w) in the formulation. The more desirable range for ST is 20–46% and the most preferred range is 30–42% (w/w). Thus, the most preferred non-aqueous injectable formulation preparation having hydroxamates or hydroxamate derivatives, comprises hydroxamate or hydroxamate derivative in an amount of 0.05 to 0.3 mg (2–10% by weight) per mg of ST (32–42% by weight).

Another embodiment of the present invention provides for a composition comprising a non-reducing carbohydrate as the bioavailability-enhancing constituent. Non-reducing carbohydrates which are useful in the compositions of the present invention include, but are not limited to: polyols and their ester derivatives. Polyols which are preferred for use in the present invention include, but are not limited to, trehalose, sucrose, mannitol and sorbitol. Trehalose (in the form of trehalose dihydrate) is particularly preferred. Preferred polyol esters include: acetate, octaacetate, and octasulfate polyol esters. Particularly preferred polyol esters include trehalose octaacetate, sucrose octaacetate, and cellobiose octaacetate.

The non-reducing carbohydrates can be added from 1 to 50% (w/w) in the formulation. The more desirable range of non-reducing carbohydrates is 5–20% (w/w) and the preferred range of is 10–15% (w/w). In formulations comprising non-reducing carbohydrates, ST can be added in an amount ranging from 10 to 50% (w/w) in the formulation. The more desirable range for ST is 20–46% (w/w) and the most preferred range is 30–40% (w/w).

In another embodiment of the present invention the bioavailability-enhancing agent is an oxo-acid salt (where an oxo-acid is an acid in which the acidic hydrogen atoms are bound to oxygen atoms). Preferred bioavailability-enhancing agents of this embodiment include: (i) monobasic sodium phosphate, $NaH_2PO_4$, dibasic sodium phosphate, $Na_2HPO_4$, or a mixture of monobasic and dibasic; (ii) monobasic potassium phosphate, $KH_2PO_4$, dibasic potassium phosphate, $K_2HPO_4$, or a mixture of monobasic and dibasic; (iii) monobasic calcium phosphate, $Ca(H_2PO_4)_2$, dibasic calcium phosphate, $CaHPO_4$, or a mixture of monobasic and dibasic; (iv) various other phosphate, sulfate or nitrate salts such as $Ca_3(PO_4)_2$, $Na_2SO_4$, and $NaNO_3$, or mixtures thereof. In a preferred embodiment the bioavailability-enhancing agent is a mixture of monobasic- and dibasic sodium phosphate, in a mixture containing more monobasic than dibasic. It is important to note that as used in this embodiment the phosphate does not act as a buffering component and does not effect the pH of the composition. The pH is determined prior to adding the phosphate and is not significantly altered by the addition of the phosphate.

The oxo-acid salt can be added from 0.5 to 30% in the formulation. The more desirable range of oxo-acid salt is 1–20% and the preferred range of oxo-acid salt is 2–10%. ST can be added from 10 to 50% in the formulation. For ST, the more desirable range is 20–40%, and the preferred range is 32–42%.

The non-aqueous carrier (excipient) can be any substance that is biocompatible and liquid or soft enough at the animal's body temperature to release the somatotropin into the animal's bloodstream at a desired rate. The carrier is usually hydrophobic and commonly organic, e.g., an oil or fat of vegetable, animal, mineral or synthetic origin or derivation. Preferably, but not necessarily, the carrier includes at least one chemical moiety of the kind that typifies "fatty" compounds, e.g., fatty acids, alcohols, esters, etc., i.e., a hydrocarbon chain, an ester linkage, or both. "Fatty" acids in this context include acetic, propionic and butyric acids through straight- or branched-chain organic acids containing up to 30 or more carbon atoms. Preferably, the carrier is immiscible in water and/or soluble in the substances commonly known as fat solvents. The carrier can correspond to a reaction product of such a "fatty" compound or compounds with a hydroxy compound, e.g., a monohydric, di-hydric, trihydric or other polyhydric alcohol, e.g., glycerol, propanediol, lauryl alcohol, polyethylene or -propylene glycol, etc. These compounds include the fat-soluble vitamins, e.g., tocopherols and their esters, e.g., acetates sometimes produced to stabilize tocopherols. Sometimes, for economic reasons, the carrier may preferably comprise a natural, unmodified vegetable oil such as sesame oil, soybean oil, peanut oil, palm oil, or an unmodified fat. Alternatively the vegetable oil or fat may be modified by hydrogenation or other chemical means which is compatible with the present invention. The appropriate use of hydrophobic substances prepared by synthetic means is also envisioned.

Compositions of this invention may also comprise, in addition to the biocompatible oil, an "antihydration agent" which term as used herein means a substance that retards hydration of a somatotropin and/or the biocompatible oil or fat and thereby further decreases and/or stabilizes the rate of release of the ST from that composition following administration to an animal. A great variety of non-toxic antihydration agents are known. By way of example there are "gelling" agents which, when dispersed, and in some cases heated to dissolve them in the oil, give the body of oil greater visco-elasticity (and therefore greater structural stability) and thereby slow down penetration of the oil by body fluids.

The exact mechanism of these agents in the present invention is not fully understood. Thus it has been observed that certain known "gelling" agents provide the desired antihydration effect even when the oil containing such an agent has not been heated to enhance their gelling effect, or when the gel formation, once formed, has been substantially eliminated (e.g. by shear forces). Also, various antihydration agents that do not have substantial ability to gel the oil are suitable for use in this invention (magnesium stearate is one example).

Exemplary antihydration agents include various polyvalent metal salts or complexes of organic acids, for instance fatty acids having from about 8 (preferably at least about 10) to about 22 (preferably up to about 20) carbon atoms, e.g. aluminum, zinc, magnesium or calcium salts of lauric acid, palmitic acid, stearic acid and the like. Such salts may be mono-, di- or tri-substituted, depending on the valence of the metal and the degree of oxidation of the metal by the acid. Particularly useful are the aluminum salts of such fatty acids. Aluminum monostearate and distearate are particularly preferred anti-hydration agents. Others that are useful include aluminum tristearate, calcium mono- and distearate, magnesium mono- and distearate and the corresponding palmitates, laurates and the like. In many embodiments, the concentration of such an antihydration agent, based on the weight of the oil plus that agent, will be advantageously between about 1% and about 10% (most typically between about 2% and about 5%), although other concentrations may be suitable in some cases.

In one embodiment of the invention the non-aqueous carrier is present at about 40% to about 90% by weight, preferably the hydrophobic carrier is present at about 40% to about 70% by weight. In one preferred embodiment the carrier is selected such that the composition is a creamy suspension at 25° C.; e.g., approximately 95% sesame oil gelled with 5% aluminum monostearate (AlMS).

Dry, solid somatotropin and dry, solid bioavailability-enhancing constituent can be prepared by lyophilization of appropriate solutions containing, respectively, the somatotropin or the BEC. Alternatively, ST or the BEC can be prepared by any other means which provides them in the proper form for use in the present invention.

The compositions of matter described for the instant invention may be prepared by any means or procedure that provides for a composition which delivers the desired enhanced bioavailability of ST at the required levels. In a preferred embodiment of the invention a certain amount of the substantially dry, solid, BEC that is effective to further increase the bioavailability of bioactive ST is mixed with the non-aqueous excipient. Next, lyophilized ST is added and the mixture is milled for an appropriate period of time in order to achieve the desired particle size and viscosity of the composition (i.e., a particle size should be small enough to provide a viscosity which allows the formulation to be useful according to the current invention). A discussion of how to achieve the desired particle size may be found in U.S. Pat. No. 5,013,713 to James Mitchell, which is herein incorporated by reference for this purpose.

While the above method is preferred, the order of adding the BEC and the ST is flexible. Furthermore, ST and some BECs can be co-lyophilized first and then this co-lyophilized product can be mixed with the non-aqueous excipient and processed as described above.

The parenteral administration of the formulations, described herein, to an animal (e.g., a mammal such as a bovine) have shown that the compositions exhibit surprisingly improved bioavailability performance characteristics for ST when compared to previously available ST formulations.

In particular, they provide a relatively more rapid, yet controlled, release during the first several days after administration without the early release becoming an exaggerated "burst" to the extent that durability of the release is unduly impaired. Typically, in terms its practical effects, the most meaningful measure of the ST release over a given period of time is calculated as the area under the curve ("AUC") illustrating the amount of ST made available by the release (e.g., the serum level of ST in the animal) and/or a physiological consequence of the release (e.g., milk produced or weight gained by an animal in which the ST has been released). Use of the invention has been found to provide a surprisingly greater AUC for measured serum concentrations, this finding is particularly true for periods of time of 14 days or more.

Even more surprising is that when the AUC represents the desirable physiological effects of ST release (e.g., the amount of milk produced daily by bovine or other lactating animals) for animals treated with the ST formulations of the present invention, the AUC is not only surprisingly greater than those of known ST/oil formulations, but also surprisingly greater than would be expected, given the magnitude of the serum ST levels present in the lactating animal. Put another way, this means that the formulations of the present invention not only provide for an enhanced release of ST, but also increase the efficacy of the released amount of ST formulation. Consequently, despite declining serum ST levels, increased milk production is sustained at a level which is surprisingly high.

Examples of the enhanced physiological effects produced by compositions of the present invention are described in examples 3–5 below. These examples describe the unexpected results of sustained elevated milk production response in lactating animals treated with the ST compositions of the instant invention. In these examples serum ST levels and milk production of animals injected with the compositions of the present invention are compared with the serum ST levels and milk production of animals, that were either untreated, or were injected with the same dose of the same somatotropin in a composition which comprised essentially the same carrier, but which lacked the bioavailability-enhancing constituent. These examples demonstrate that the animals injected with the ST compositions of the present invention have an unexpectedly high and sustained level of milk production.

Thus the compositions of the instant invention provide both higher serum ST levels and a more sustained elevated milk production response, per milligram of ST injected, than provided by previously know compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Examples of Representative Compositions

Table 1 provides a tabulated summary of exemplary compositions for enhanced bioavailability of ST formulations. The weight percent of the bioavailability-enhancing factor and somatotropin are indicated as is the non-aqueous excipient used.

TABLE 1

| Bioavailability-Enhancing Agent (BEC) | % BEC | % ZnbST[1] | Hydrophobic Carrier |
|---|---|---|---|
| Histidine-HCl | 3 | 42 | SO:AlMS 95:5[2] |
| Histidine-HCl | 5 | 38 | SO:AlMS 95:5 |
| Histidine-HCl | 4.5 | 43 | SO:AlMS 95:5 |
| Histidine-HCl | 1 | 38 | SO:AlMS 95:5 |
| Histidine-HCl | 2.5 | 38 | SO:AlMS 95:5 |
| Histidine-HCl | 10 | 38 | SO:AlMS 95:5 |
| Polyhistidine-HCl | 5 | 38 | SO:AlMS 95:5 |
| Arginine | 5 | 38.5 | SO:AlMS 95:5 |
| Histidine free base | 5 | 38.4 | SO:AlMS 95:5 |
| Glutamic Acid | 5 | 38 | SO:AlMS 95:5 |
| Monosodium Glutamate | 5 | 38 | SO:AlMS 95:5 |
| Glycine | 5 | 38 | SO:AlMS 95:5 |
| Methionine | 5 | 38 | SO:AlMS 95:5 |
| Tryptophan | 5 | 38 | SO:AlMS 95:5 |
| Imidazole | 5 | 38 | SO:AlMS 95:5 |
| Imidazole-HCl | 5 | 38 | SO:AlMS 95:5 |
| Bufexamac acid | 5 | 38 | SO:AlMS 95:5 |
| Histidine Hydroxamate | 5 | 38 | SO:AlMS 95:5 |
| Salicyl hydroxamic acid | 5 | 38 | SO:AlMS 95:5 |
| Caprylohydroxamic acid | 5 | 38 | SO:AlMS 95:5 |

TABLE 1-continued

| Bioavailability-Enhancing Agent (BEC) | % BEC | % ZnbST[1] | Hydrophobic Carrier |
|---|---|---|---|
| Suberohydroxamic acid | 5 | 38 | SO:AlMS 95:5 |
| Trehalose dihydrate | 5 | 34 | SO:AlMS 95:5 |
| Trehalose dihydrate | 10 | 34 | SO:AlMS 95:5 |
| Trehalose dihydrate | 15 | 34 | SO:AlMS 95:5 |
| Trehalose dihydrate | 14 | 31 | SO:AlMS 95:5 |
| Trehalose dihydrate | 5 | 38.5 | SO:AlMS 95:5 |
| Trehalose octaacetate | 5 | 38 | SO:AlMS 95:5 |
| Sucrose | 15 | 33 | SO:AlMS 95:5 |
| Sucrose octaacetate | 4 | 38 | SO:AlMS 95:5 |
| Sucrose octasulfate | 5 | 38 | SO:AlMS 95:5 |
| Monobasic and dibasic sodium phosphate; 6:4 molar ratio | 5 | 38 | SO:AlMS 95:5 |
| Monobasic sodium phosphate | 5 | 38.3 | SO:AlMS 95:5 |
| Dibasic sodium phosphate | 5 | 38.3 | SO:AlMS 95:5 |
| Sodium Sulfate | 5 | 38.3 | SO:AlMS 95:5 |
| Sodium Nitrate | 5 | 38.3 | SO:AlMS 95:5 |
| Monobasic and dibasic potassium phosphate; 6:4 molar ratio | 5 | 38.3 | SO:AlMS 95:5 |
| Monobasic and dibasic calcium phosphate; 6:4 molar ratio | 5 | 38.3 | SO:AlMS 95:5 |
| Potassium Citrate | 5 | 38.3 | SO:AlMS 95:5 |
| Ammonium Sulfate | 5 | 38.3 | SO:AlMS 95:5 |

[1]ZnbST = Zinc bound bovine somatotropin.
[2]SO:AlMS 95:5 = sesame oil (95%):aluminum monostearate (5%)

Example 2

Rat Growth Studies in Rodents for a Variety of Compositions

A rat growth assay was used to measure the biological potency of ST containing formulations. As used here the term "biological potency" denotes the capacity of the ST formulations to accelerate weight gain in rodents treated therewith.

Rodents were injected subcutaneously with 25 mg of bST mixed with the various BECs described in Table 2 and the rodent daily weights were followed for 15 days.

Table 2 lists the formulation, the relative potency (versus POSILAC®), and the 95% confidence interval for relative potency.

TABLE 2 bST formulation relative potency in rodents

| Description of Composition | Relative Potency | Lower Limit | Upper Limit |
|---|---|---|---|
| POSILAC ® | 100.00 | 98.43 | 101.57 |
| 38.5% ZnbST + 4% sucrose octaacetate | 121.21 | 119.24 | 123.17 |
| 40.5% ZnbST + 8% sucrose octaacetate | 122.35 | 120.57 | 124.13 |
| 38.5% ZnbST + 8% sucrose octaacetate | 128.61 | 126.73 | 130.49 |
| 40.3% ZnbST + 8% sucrose octaacetate in SO[1] | 122.80 | 120.87 | 124.74 |
| 38.5% ZnbST + 5% trehalose octaacetate | 136.88 | 134.95 | 138.81 |
| 33% ZnbST + 10% trehalose octaacetate in SO/AlMS in SO/AlMS (2.5%)[2] | 100.96 | 99.13 | 102.79 |
| 38.5% ZnbST + 5% sucrose octasulfate | 109.27 | 107.41 | 111.13 |
| 34.6% ZnbST + 10% NaP[3,4] in palm oil (no AlMS) | 125.34 | 123.54 | 127.14 |
| 38.3% ZnbST + 5% NaP | 122.47 | 120.69 | 124.25 |
| 38.3% ZnbST + 5% NaP (monobasic) | 114.12 | 112.34 | 115.91 |
| 38.3% ZnbST + 5% NaP (dibasic) | 129.14 | 127.19 | 131.09 |

TABLE 2-continued bST formulation relative potency in rodents

| Description of Composition | Relative Potency | Lower Limit | Upper Limit |
| --- | --- | --- | --- |
| 38.3% ZnbST + 5% potassium phosphate (6:4)[4] | 130.89 | 129.04 | 132.74 |
| 38.3% ZnbST + 5% calcium phosphate (6:4) | 116.56 | 114.88 | 118.25 |
| 46.5% Zuless bST[6] (pH 10.5) + 5% NaH$_2$PO$_4$ in SO | 123.86 | 122.16 | 125.57 |
| 46.5% Znless bST (pH 10.5) + 5% Histidine-HCl in SO | 126.37 | 124.27 | 128.46 |
| 46.5% abST[5] (pH 10.7) + 5% NaH$_2$PO$_4$ in SO | 126.02 | 124.14 | 127.91 |
| 49.2% abST (pH 8.9) in SO | 137.73 | 135.91 | 139.55 |
| 38.3% Znless bST[6] (pH 8.1) in SO | 139.74 | 137.64 | 141.85 |

[1]SO = Sesame Oil
[2]SO/AlMS (2.5%) = sesame oil 97.5%:aluminum monostearate 2.5%
[3]NaP = sodium phosphate.
[4](6:4) = a 6 to 4 molar ratio mixture of the monobasic to dibasic form of the salt.
[5]abST = alanine bovine somatotropin (has alanine as the N-terminal amino acid).
[6]Znless bST = bST which does not have zinc bound

Example 3

Efficacy of Formulations Comprising histidine-HCl as the Bioavailability Enhancing Constituent The performance of the formulation in the animals which received an injection of this formulation was determined by measuring the concentration of bovine somatotropin (bST) in the animal's serum over time, and then calculating the area under the curve (AUC) for a concentration vs. time plot. These studies clearly demonstrated that the addition of histidine-HCl to the formulation surprisingly improved the bST bioavailability, as measured by serum bST AUCs in animals such as rodents, calves or dairy cows. The formulations also exhibited dramatic improvements as measured by weight gain response in rodents and by increased milk production in dairy cows.

The performance improvement of the formulation when compared with POSILAC® is illustrated by three lots. Lot NBP6569246 contains 42% (dry solid) Zinc bovine somatotropin (ZnbST) and 3% (dry solid) histidine-HCl, and lots NBP6207806B and NBP6996911 contain 38% (dry solid) ZnbST and 5% (dry solid) histidine-HCl. Both dry solids are suspended in the typical POSILAC® excipient, i.e., 95% sesame oil gelled with 5% aluminum monostearate (AlMS).

For the present example, all bST formulations were administered subcutaneously. The dosage for pharmicokinetic studies in rodents was 15 mg of bST. For the bovine studies the dosage was 500 mg bST.

Figure 2:
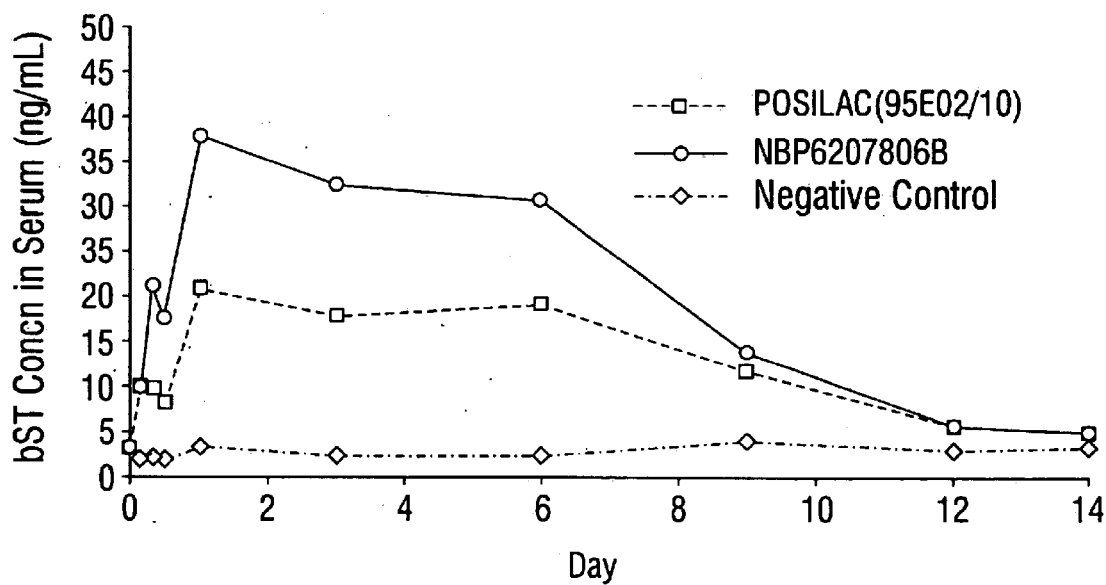
FIG. 2 is a graph showing the serum bST levels over time in calves treated with a bST composition containing histidine-HCl as the bioavailability-enhancing constituent.

The mean bST serum concentrations in rodents and calves receiving these formulations were measured over a 14 day period and are shown in FIGS. 1 and 2, respectively. Compared to POSILAC®, a surprisingly elevated and sustained serum bST concentration was observed with the formulations containing histidine-HCl.

Figure 3:
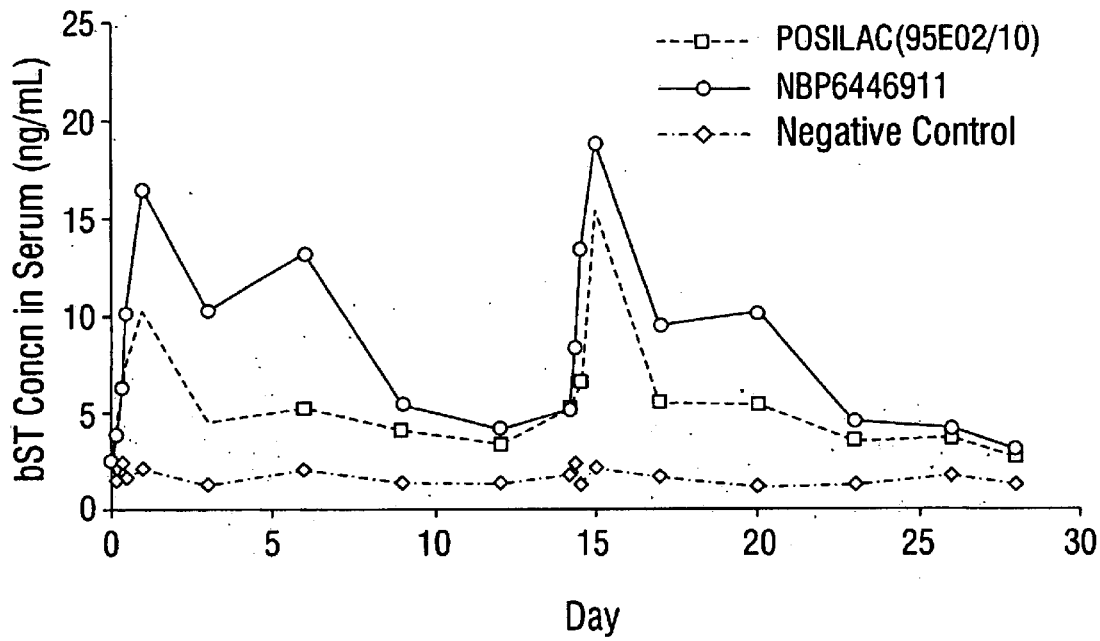
FIG. 3 is a graph showing the serum bST levels over time in cows treated with a bST composition containing histidine-HCl as the bioavailability-enhancing constituent.

As shown in FIG. 3, concentration of serum bST increased over both POSILAC® and the negative control after injection of the suspension formulations in dairy cows. Over two 14-day cycles, the relative bST AUC (the histidine-HCl formulation AUC/POSILAC® AUC) is calculated to be 1.7, indicating that the presence of histidine-HCl in the formulation dramatically improves the bST release into the circulatory system and results in a 70% bST increase in bioavailability in target animals compared with POSILAC®.

Following injection of the histidine-HCl formulations, milk production increased and continued to be elevated with respect to both POSILAC® and the negative control throughout each of six 14-day injection cycles. A sustained, elevated milk response over six 14-day cycles was shown in trials using dairy cows. The increase in milk production over six 14-day cycles, was 4 pounds more per day than achieved using POSILAC® and is surprisingly high as seen in FIG. 4 which represents the average of six 14-day treatment periods.

Figure 4:
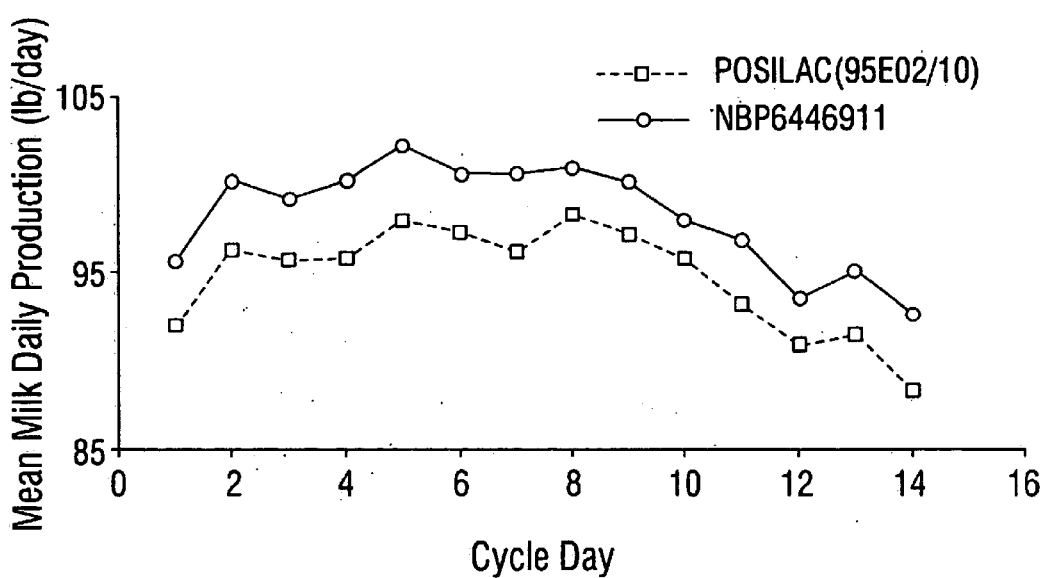
FIG. 4 is a graph showing the mean daily milk production, over time, in lactating cows treated with either a bST composition comprising histidine-HCl as the bioactivity-enhancing constituent or POSILAC®.

Particularly surprising is the observation that increased milk production is sustained, in animals treated with the histidine-HCl containing ST formulations, despite the fact that the serum bST levels for animals treated with the POSILAC® formulation, the bST/histidine-HCl formulation, or the negative control, are nearly identical at the end of each 14-day cycle compare the day 14 time points in FIGS. 3 and 4). These data clearly demonstrate a sustained elevated milk production response for the animals treated with the bST/histidine-HCl formulations.

Example 4

Efficacy of Formulations Comprising a Non-Reducing Carbohydrate as the Bioavailability Enhancing Constituent Formulations comprising bST and non-reducing carbohydrate bioavailability-enhancing constituents have been found to provide surprisingly elevated release of bST in laboratory rodents, calves and dairy cattle as measured by a) increased serum bST levels in the animals; and b) resulting weight gains in rodents, and c) elevated milk production in cows, for over 14 days after administration.

The performance improvement of the carbohydrate containing formulations of the instant invention when compared with POSILAC® is illustrated by two lots (NBP 6393203 & 6446921). Those lots contains 31–33% Zinc bovine somatotropin (ZnbST) and 14–15% trehalose dihydrate (both suspended) in the typical POSILAC® excipient, i.e., 95% sesame oil gelled with 5% aluminum monostearate (AlMS).

Figure 5:
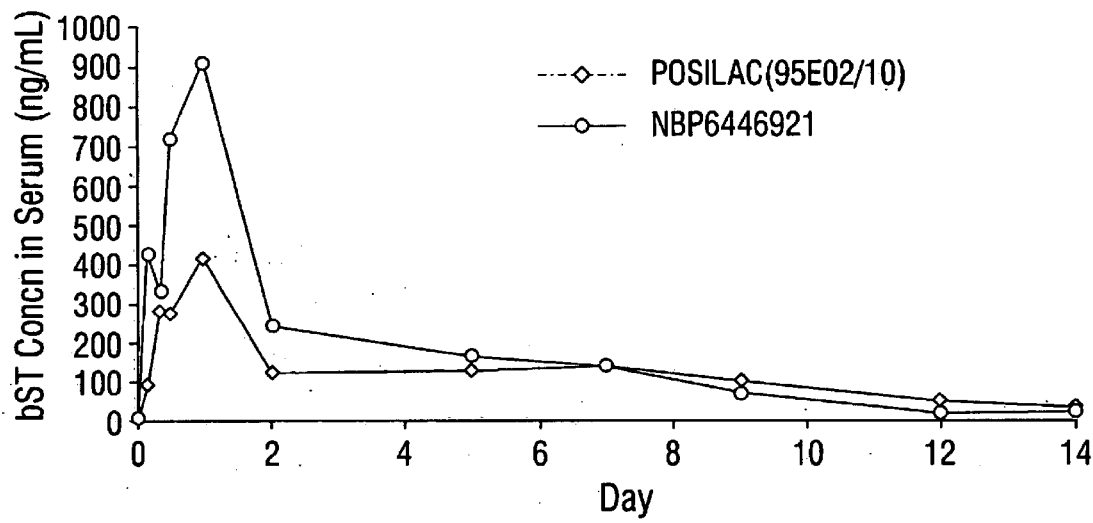
FIG. 5 is a graph showing the serum bST levels over time in rodents treated with a bST composition which contained trehalose dihydrate as the bioavailability-enhancing constituent.
Figure 6:
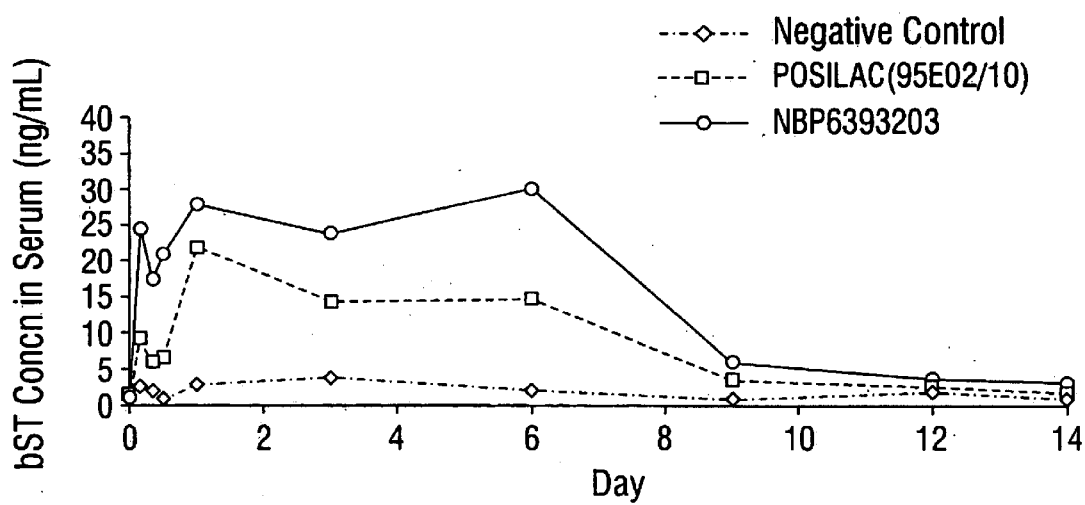
FIG. 6 is a graph showing the serum bST levels over time in calves treated with a bST composition containing trehalose dihydrate as the bioavailability-enhancing constituent.

The dosages of bST administered were the same as those described in Example 3. The mean bST serum concentrations over 14 days in rodents and calves after receiving formulations are shown in FIGS. 5 and 6, respectively. Compared to POSILAC®, a remarkably sustained and elevated serum bST concentration has been observed in animals treated with the non-reducing carbohydrate containing formulations.

Figure 7:
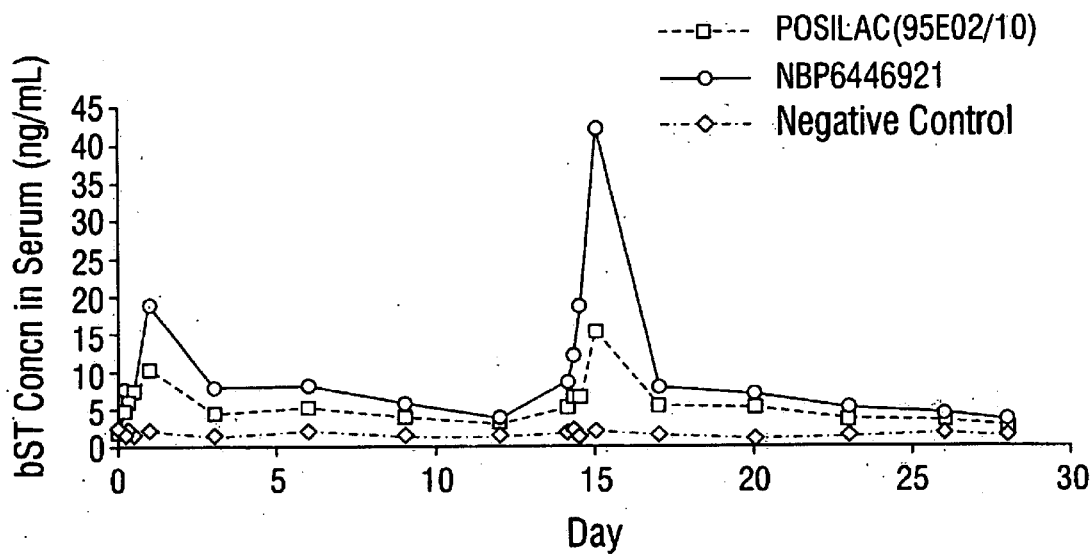
FIG. 7 is a graph showing the serum bST levels over time in cows treated with a bST composition containing trehalose dihydrate as the bioavailability-enhancing constituent.

As shown in FIG. 7, the concentration of serum bST was increased, when compared with both POSILAC® and the negative control, following injection of the non-reducing carbohydrate containing formulations in dairy cows. The bST area-under-the-curve (AUC), the total area under a plot of serum bST concentration vs time after a single dose administration, is a measurement of bST bioavailability. Over two 14-day cycles, the relative bST AUC (the carbohydrate containing formulation AUC over POSILAC® AUC) is calculated to be 1.8, indicating that the presence of carbohydrate in the formulation improves the bST release into the circulatory system and results in a 80% bST increase in bioavailability in target animals compared to POSILAC®.

Following injection of the carbohydrate containing formulation, milk production increased and continued to be elevated, with respect to the levels measured for both POSILAC® treated and the negative control animals, throughout each of six 14-day injection cycles. The sustained elevated milk production over six 14-day cycles was shown in trials using dairy cows. For dairy cows treated with the carbohydrate-containing ST composition, the milk yield, throughout six 14-day cycles, was 5 pounds per day greater than that resulting from treatment with POSILAC®, and is surprisingly high as shown in FIG. 8 which represents the average of six 14-day treatment periods.

Figure 8:
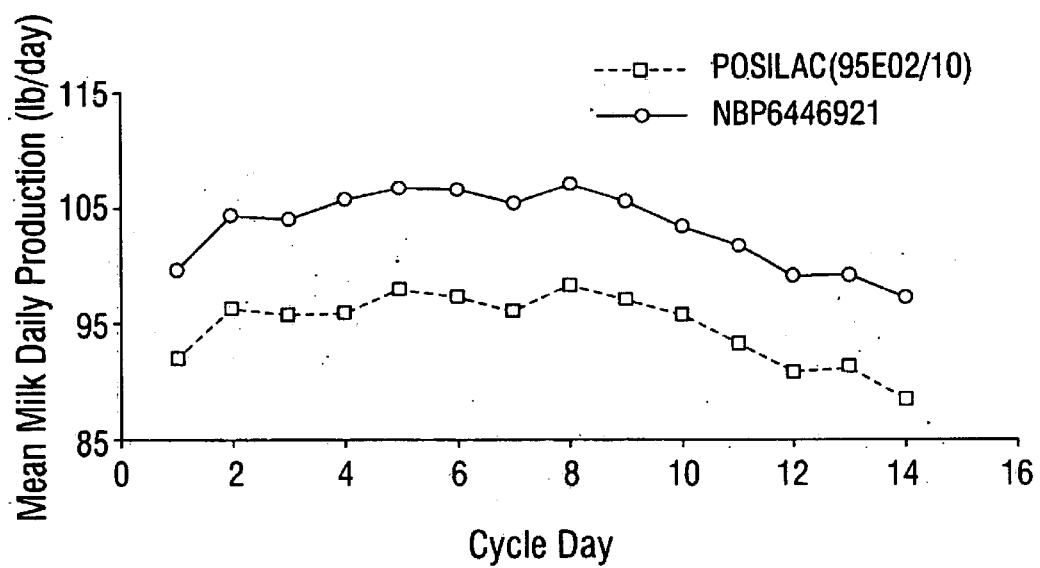
FIG. 8 is a graph showing the mean daily milk production, over time, in lactating cows treated with either a bST composition comprising trehalose dihydrate as the bioactivity-enhancing constituent or POSILAC®.

Particularly surprising is the observation that increased milk production is maintained in animals treated with the trehalose dihydrate containing formulation, despite the fact that serum bST levels, in cows treated with POSILAC®, the bST/trehalose dihydrate formulation, or the negative control are nearly identical at the end of each 14-day cycle (compare the day 14 time points in FIGS. 7 and 8). These data clearly demonstrate a sustained elevated milk production response for the animals treated with the bST/trehalose dihydrate formulations.

Example 5

Efficacy of Formulations Comprising an Oxo-Acid salt as the Bioavailability Enhancing Constituent Serum bST levels in an animal that has received an injection of enhanced bST formulations containing an oxo-acid salts were determined by measuring the animal's serum bST concentrations over time and then calculating the area under the curve (AUC) for a concentration vs time plot. Addition of certain salts of oxo-acids has shown surprisingly improved results with respect to the bST bioavailability, as measured by serum bST AUCs in animals such as rodents, calves or dairy cows. Also improved was the performance of the formulation in rodents as measured by weight gain response and in dairy cows as measured by milk production.

The improvement in performance of the bST/oxo-acid salt formulations when compared with POSILAC® are illustrated by two lots (NBP 6207810A & 6446916). Those lots contains 38% zinc bovine somatotropin (ZnbST) and 5% sodium phosphate (at 6:4 molar ratio of monobasic to dibasic) in the typical POSILAC® excipient, i.e., 95% sesame oil gelled with 5% aluminum monostearate (AlMS).

Figure 9:
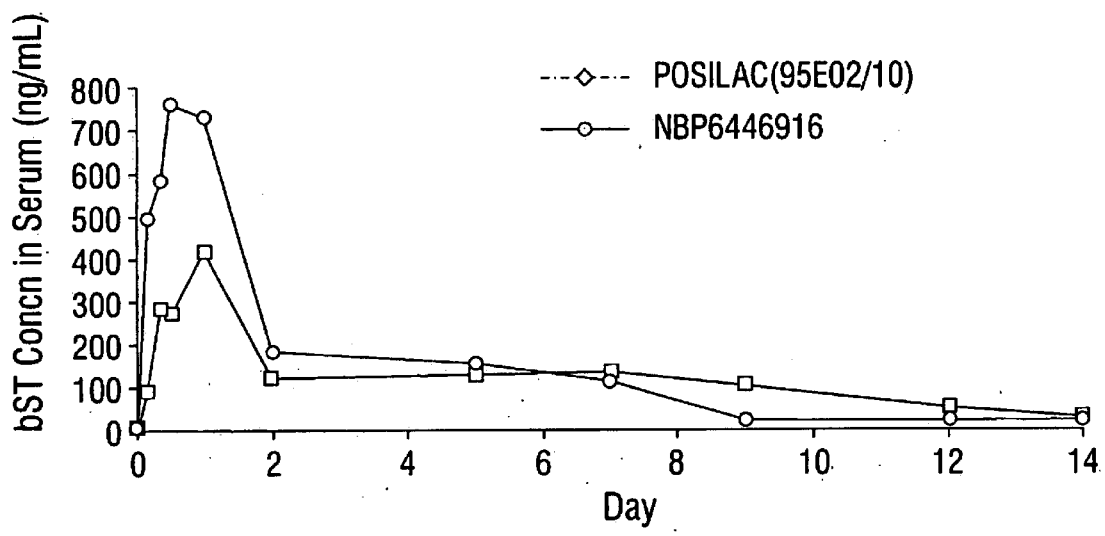
FIG. 9 is a graph showing the serum bST levels over time in rodents treated with a bST composition which contained a mixture of monobasic- and dibasic sodium phosphate as the bioavailability-enhancing constituent.
Figure 10:
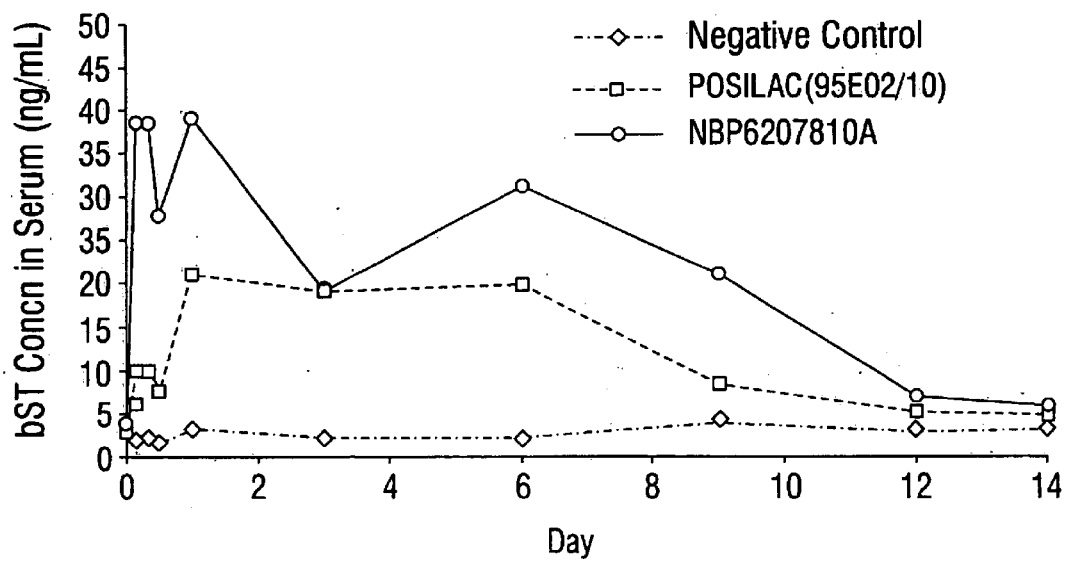
FIG. 10 is a graph showing the serum bST levels over time in calves treated with a bST composition containing monobasic- and dibasic sodium phosphate as the bioavailability-enhancing constituent.

The dosages of bST administered were the same as those described in Example 3. The mean bST serum concentrations in rodents and calves were measured over a 14 day period after receiving these formulations, these are shown in FIGS. 9 and 10, respectively. When compared to POSILAC®, a surprisingly sustained and elevated serum bST concentration has been observed with these formulations.

Figure 11:
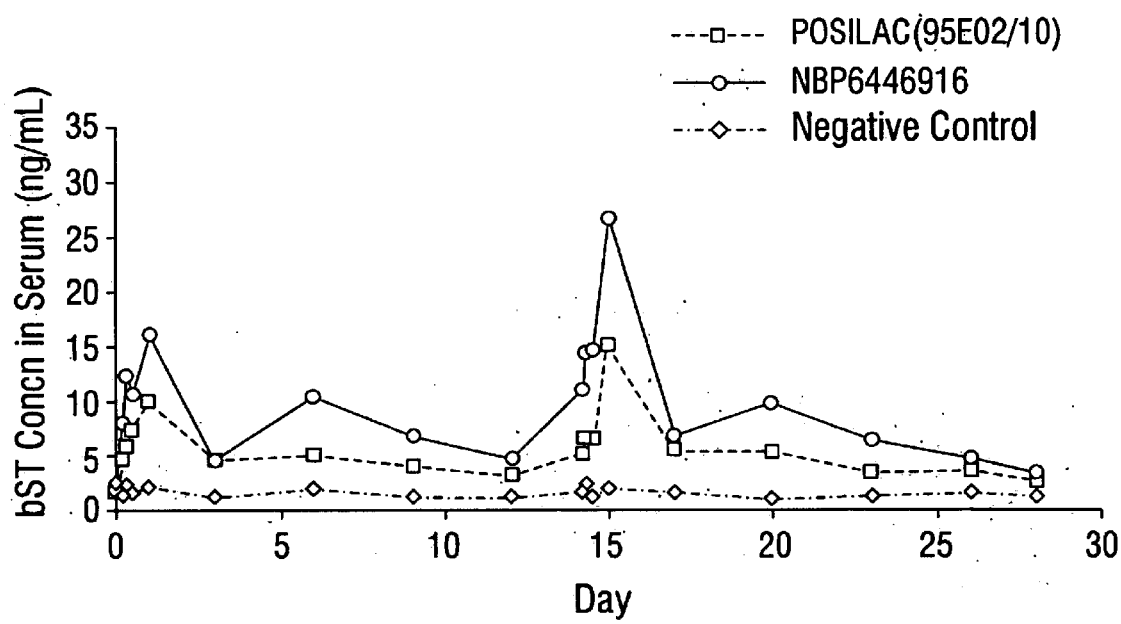
FIG. 11 is a graph showing the serum bST levels over time in cows treated with a bST composition containing monobasic- and dibasic sodium phosphate as the bioavailability-enhancing constituent.

As shown in FIG. 11, the concentration of serum bST concentration in dairy cows injected with the bST/oxo-acid salt formulation was increased with respect to both POSILAC® and the negative control. Over two 14-day cycles, the relative bST AUC (the new formulation AUC over POSILAC® AUC) is 1.8, indicating that the presence of sodium phosphate salt mixture in the formulation enhances the bST release into the circulatory system and results in a 80% increase in bST bioavailability in target animals when compared to POSILAC®.

Following injection of the oxo-acid containing formulation, milk production increased and continued to be elevated with respect to both POSILAC® and the negative control throughout each of six 14-day injection cycles. The observed increase in overall milk yield, over six 14-day cycles, was 6 pounds per day greater than that of lactating cattle treated with POSILAC® and is surprisingly high as seen in FIG. 12 which represents the average of six 14-day treatment periods.

Figure 12:
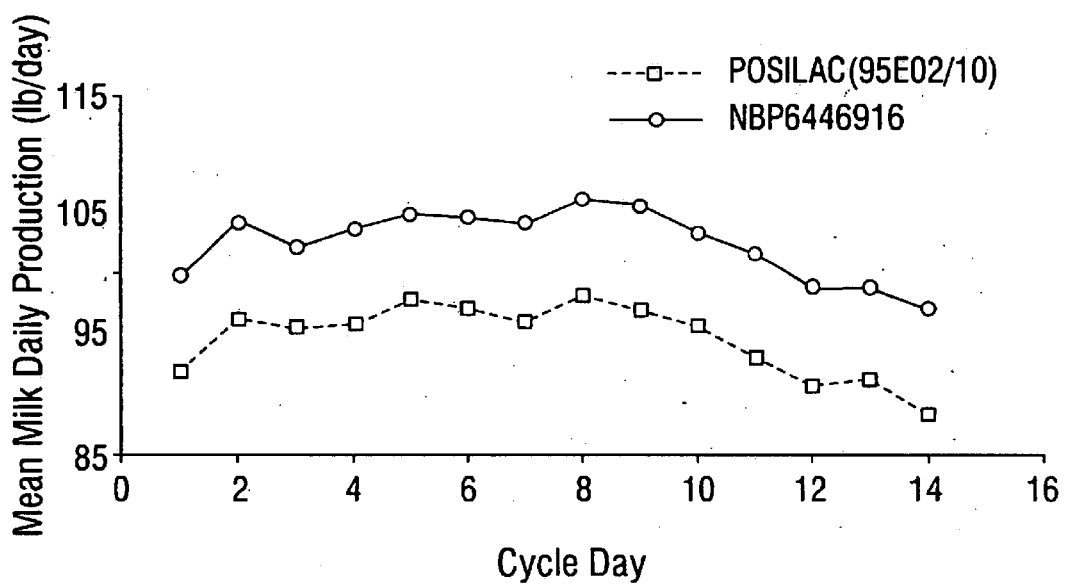
FIG. 12 is a graph showing the mean daily milk production, over time, in lactating cows treated with either a bST composition comprising a mixture of monobasic- and dibasic sodium phosphate as the bioactivity-enhancing constituent or POSILAC®.

Particularly surprising is the observation that increased milk production is maintained in animals treated with the sodium phosphate containing formulation, despite the fact that serum bST levels, in cows treated with POSILAC®, the bST/sodium phosphate formulation (lot NBP66446916), or the negative control are nearly identical at the end of each 14-day cycle (compare the day 14 time points in FIGS. 11 and 12). These data clearly demonstrate a sustained elevated milk production response for the animals treated with the bST/sodium phosphate formulations.

Example 6

Pharmicokinetic Studies in Rodents for a Variety of Compositions

Rodents were injected subcutaneously with 15 mg of bST (prepared with the various BECs described in Table 1) according to the following protocol.
Test Subjects:
Mature female Sprague-Dawley rats, 12–13 weeks of age, ~250 g.
Control Group:
Six (6) rats treated with reference standard material.
Treated Groups:
Six (6) rats per test article (formulation lot), randomly assigned. Animals were assigned to treatment groups using a completely randomized design according to body weight on Day −1 or Day 0 prior to treatment initiation. A weight range of 250 +/−20 gram was used.
Test Articles:
POSILAC®, as a positive control, and various bST formulations were studied.
Section B: Weighing, Dosing, Blood Collection, and Sample Shipment
Weighing:
Animals were weighed on Day −1 or Day 0 for randomization and treatment assignment. A final weight was taken on Day 14 following the final blood sample collection.
Route of Injection:
Subcutaneous (SC) injection in the dorsal suprascapular region. Injections were administered with 1 cc tuberculin syringes with 18 G 1.5-inch needles for all formulations.
Dose Volumes:
15 mg of bST with the dose volume of 0.04 ml were administered to each rat on Day 0. A fill volume of ~0.08 ml was prepared to adjust for the amount of formulation remaining in the needle following the injection. The time of injection was recorded for each individual rat. Syringes were weighed both prior to and following injection to determine the weight of the protein injected.

Blood Collection:

Blood samples were collected via retro-orbital bleeds, using alternating eyes at the various time-points, following anesthesia with $CO_2/O_2$ (80/20) gas. EDTA coated or non-coated micro-hematocrit capillary tubes were used for the blood collections. The whole blood was transferred to blood plasma separator tubes (Microtainer® with EDTA, lavender; MFG# BD5960). The blood was then centrifuged at 6000 g for 10 minutes at room temperature. Samples were stored frozen at −20° C.

Blood Volumes:

It was necessary to obtain a minimum of 200 µl of whole blood at each time point from each rat in order to have 100 µl of plasma. A total volume of 300 µl of whole blood is preferable to ensure an adequate plasma volume.

Blood Collection Time Points:

Blood samples were collected at 11 time points, 7 different time points for each rat, following the sampling scheme outlined in the Rat Blood Sampling Schedule (below). The time of collection were recorded for each individual rat.

Blood Collection Time Points

Day 0, prior to injection 4, 8, and 12 hours post-injection (after the injection)

Day 1 (24 hr)
Day 2 (48 hr)
Day 5 (120 hr)
Day 7 (168 hr)
Day 9 (216 hr)
Day 12 (288 hr)
Day 14 (336 hr)

Note: All blood collections were within +/− one (1) hour.

Rat Blood Sampling Schedule:

| Time | Rat# 1 | 2 | 3 | 4 | 5 | 6 |
|---|---|---|---|---|---|---|
| 0 | X | X | X | X | X | X |
| 4 hr | X | | X | | X | |
| 8 hr | X | X | | X | | |
| 12 hr | | X | X | | | X |
| Day 1 (24 hr) | | | | X | X | X |
| Day 2 (48 hr) | X | X | X | | | |
| Day 5 (120 hr) | | X | | X | X | X |
| Day 7 (168 hr) | X | | X | X | X | |
| Day 9 (216 hr) | | X | | X | | X |
| Day 12 (288 hr) | X | | X | | X | X |
| Day 14 (336 hr) | X | X | X | X | X | X |

Note:
This scheme gives seven (7) bleeds per rat over a 14 day period.
Serum samples were collected and analyzed for bST levels.

All of the compositions and methods disclosed and claimed herein can be made and executed without undue experimentation in light of the present disclosure. While the compositions and methods of this invention have been described in terms of preferred embodiments, it will be apparent to the skilled artisan that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Christensen et al., WO 97/03692; February/1997; A61K 38/27, 33/30
Furguson et al., U.S. Pat. No. 4,977,140; December/1990; 514/12
Hamilton et al., U.S. Pat. No. 4,816,568; March/1989; 530/399
Kim et al., U.S. Pat. No. 5,520,927; May/1996; 424/450
Kim et al., U.S. Pat. No. 5,744,163; April/1998; 424/489
Krivi, G. G., U.S. Pat. No. 5,399,489; March/1995; 435/172.3
Magruder et al., U.S. Pat. No. 5,034,229; July/1991; 424/422
Martin, EP 0 216 485; April/1987; C 07 G 15/00
Mitchell, U.S. Pat. No. 5,739,108; April/1998; 514/12
Pikal et al., U.S. Pat. No. 5,612,315; March/1997; 514/21
Raman et al., U.S. Pat. No. 5,356,635; October/1994; 424/484
Raman et al., WO 93/13792; July/1993
Seeley et al., WO 93/19773; October/1993
Sivaramakrishnan et al., U.S. Pat. No. 5,219,572; June/1993; 424/438
Sørensen et al., WO 93/12812; July/1993; A61K 37/36
Sørensen et al., U.S. Pat. No. 5,849,704; December/1998; 514/12
Steber et al., EP 0 523 330 Al; January/1993; A61K 9/00
Storrs et al., U.S. Pat. No. 5,986,073; November/1999; 530/419
Tyle, U.S. Pat. No. 4,857,506; August/1989; 514/12
Viswanathan et al., U.S. Pat. No. 4,917,685; April/1990; 604/891.1

What is claimed is:

1. A composition of matter, comprising:
somatotropin and a constituent that enhances bioavailability of the somatotropin in an animal to which the composition of matter has been administered parenterally;
wherein the bioavailability enhancing constituent is selected from the group consisting of one or a mixture of both of the following:
a) one or more non-reducing carbohydrate(s) and
b) one or more oxo-acid salt(s);
wherein the somatotropin and the bioavailability enhancing constituent are suspended in a substantially non-aqueous hydrophobic carrier, wherein the somatotropin is present at from about 10 to about 50% by weight of the composition, wherein the bioavailability enhancing constituent is present at from about 1% to about 20% by weight of the composition, and
wherein the composition is fluidly injectable at 25° C.

2. The composition of matter of claim 1 wherein the somatotropin is human, equine, bovine, or porcine.

3. The composition of matter of claim 1, wherein the bioavailability enhancing constituent is non-reducing carbohydrate selected from the group consisting of: at least one polyol, at least one carbohydrate ester, and mixtures thereof.

4. The composition of matter of claim 1, wherein the bioavailability enhancing constituent comprises non-reducing carbohydrate; wherein the non-reducing carbohydrate is polyol present at from about 5% to about 20% by weight of the composition.

5. The composition of claim 1, wherein the bioavailability enhancing constituent comprises at least one oxo-acid salt.

6. The composition of claim 5, wherein the oxo-acid salt is selected from one or a mixture of two or more of the following: monobasic sodium phosphate, dibasic sodium phosphate, monobasic potassium phosphate, dibasic potassium phosphate, monobasic calcium phosphate, dibasic calcium phosphate, sodium nitrate, dibasic sodium sulfate, and mixtures thereof.

7. The composition of matter of claim 1, wherein the hydrophobic carrier comprises an oil or a fat.

8. The composition of matter of claim 1,
wherein the somatotropin is a zinc salt of bovine somatotropin present at from about 32% to about 42% by weight;
wherein, the bioavailability enhancing constituent is a mixture of monobasic sodium phosphate and dibasic sodium phosphate salts, wherein the molar ratio of monobasic sodium phosphate to dibasic sodium phosphate is about 6 to 4, present at from about 2% to about 10% by weight.

9. A method of making a composition of matter, comprising:
somatotropin and a bioavailability enhancing constituent;
wherein the bioavailability enhancing constituent is selected from the group consisting of one or a mixture of both of the following:
a) one or more non-reducing carbohydrate(s) and
b) one or more oxo-acid salt(s);
wherein the somatotropin and the bioavailability enhancing constituent are suspended in a substantially non-aqueous hydrophobic carrier, wherein the somatotropin is present at from about 10 to about 50% by weight of the composition, wherein the bioavailability enhancing constituent is present at from about 1% to about 20% by weight of the composition, and
wherein the composition is fluidly injectable at 25° C.;

the method comprising:
providing the somatotropin as a lyophilized dry solid, the bioavailability enhancing constituent, as a dry solid, and the hydrophobic carrier;
mixing the bioavailability enhancing constituent with the hydrophobic carrier, to produce a first suspension; and,
mixing the somatotropin with the first suspension to produce a second suspension.

10. A composition of matter, comprising:
somatotropin and a bioavailability enhancing constituent;
wherein the bioavailability enhancing constituent comprises one or more non-reducing carbohydrates;
wherein the somatotropin and the bioavailability enhancing constituent are suspended in a substantially non-aqueous hydrophobic carrier, wherein the somatotropin is present at from about 10 to about 50% by weight of the composition, wherein the bioavailability enhancing constituent is present at from about 1% to about 20% by weight of the composition, and
wherein the composition is fluidly injectable at 25° C.

11. A composition of matter, comprising:
somatotropin and a bioavailability enhancing constituent;
wherein the bioavailability enhancing constituent comprises one or more oxo-acid salts;
wherein the somatotropin and the bioavailability enhancing constituent are suspended in a substantially non-aqueous hydrophobic carrier, wherein the somatotropin is present at from about 10 to about 50% by weight of the composition, wherein the bioavailability enhancing constituent is present at from about 1% to about 20% by weight of the composition, and
wherein the composition is fluidly injectable at 25° C.

* * * * *